(12) United States Patent
Paul, Jr.

(10) Patent No.: US 9,149,279 B2
(45) Date of Patent: Oct. 6, 2015

(54) OCCLUDING DEVICE

(71) Applicant: COOK MEDICAL TECHNOLOGIES LLC, Bloomington, IN (US)

(72) Inventor: Ram H. Paul, Jr., Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

(21) Appl. No.: 14/556,666

(22) Filed: Dec. 1, 2014

(65) Prior Publication Data

US 2015/0088189 A1   Mar. 26, 2015

Related U.S. Application Data (62) Division of application No. 13/059,717, filed as application No. PCT/US2009/054189 on Aug. 18, 2009, now Pat. No. 8,945,170.

(60) Provisional application No. 61/089,794, filed on Aug. 18, 2008.

(51) Int. Cl.
    *A61M 29/00*     (2006.01)
    *A61B 17/12*     (2006.01)
    *C07D 471/04*    (2006.01)

(52) U.S. Cl.
    CPC ....... *A61B 17/12177* (2013.01); *A61B 17/1219* (2013.01); *A61B 17/12022* (2013.01); *A61B 17/12109* (2013.01); *A61B 17/12172* (2013.01); *C07D 471/04* (2013.01); *A61B 2017/12054* (2013.01)

(58) Field of Classification Search
    CPC ............. A61B 17/12177; A61B 17/12022; A61B 17/12109; A61B 17/12172; A61B 17/1219; A61B 2017/12054
    USPC ........... 606/127, 159, 200, 191; 623/1.36, 623/23.72; 604/104–107
    See application file for complete search history.

(56) References Cited

U.S. PATENT DOCUMENTS

| | | |
|---|---|---|
| 2003/0195555 A1 | 10/2003 | Khairkhahan et al. |
| 2004/0220610 A1* | 11/2004 | Kreidler et al. ............... 606/200 |
| 2007/0066993 A1 | 3/2007 | Kreidler |

* cited by examiner

*Primary Examiner* — Victor Nguyen
*Assistant Examiner* — Kevin Everage
(74) *Attorney, Agent, or Firm* — Brinks Gilson & Lione (57) ABSTRACT

An occluding device is provided for occluding fluid flow through a lumen of a body vessel. The occluding device includes an expandable tubular body having a tubular wall defining a lumen formed therethrough. The tubular wall has a proximal end extending to a distal end along a longitudinal axis of the tubular body. A plurality of longitudinal slits is formed through the tubular wall to define a plurality of flexible strips bound by a proximal non-slit portion and a distal non-slit portion. A plurality of barbs is disposed on the flexible strips. The tubular body is configured to open radially to engage the barbs with the vessel wall defining an expanded state and to collapse along the longitudinal axis to draw the vessel wall radially inward defining a collapsed state. Occluding material is housed within the lumen of the tubular body and the occluding material is configured to move between a collapsed state and an expanded state with the tubular body.

20 Claims, 8 Drawing Sheets

OCCLUDING DEVICE

CROSS-REFERENCE TO RELATED APPLICATIONS

This application claims priority to U.S. Provisional Patent Application Ser. No. 61/089,794, filed Aug. 18, 2008, entitled "OCCLUDING DEVICE AND METHOD OF OCCLUDING FLUID FLOW THROUGH A BODY VESSEL," and is a divisional application of U.S. patent application Ser. No. 13/059,717, filed Aug. 18, 2009, entitled "OCCLUDING DEVICE," the entire contents of both which are incorporated herein by reference.

FIELD OF INVENTION

The present invention relates to medical devices. More particularly, the invention relates to occluding devices and methods of occluding fluid flow through a body vessel.

BACKGROUND OF THE INVENTION

Vaso-occlusive devices are surgical implants that are placed within the vasculature of the human body, typically via a catheter, either to block the flow of blood through a vessel making up that portion of the vasculature by formation of an embolus, or to form such an embolus within an aneurysm stemming from the vessel. A common vaso-occlusive device is an embolization coil configured as a helically wound coil that is introduced to a treatment site in the body. For example, the helically wound coil may have a spiral, tornado, or stacked configuration. Spider-like devices are used to contain coils when vessels are large and/or flow is high. Synthetic fibers can be included in the coil to assist with activation of the clotting cascade. Typically, the procedure utilizing the embolization coil includes delivering the coil portion of the device to the treatment site via catheter, wherein the coil separates from the device and remains in the body, forming the desired obstruction. The pusher wire and catheter are then retrieved from the body.

Figure 1A:
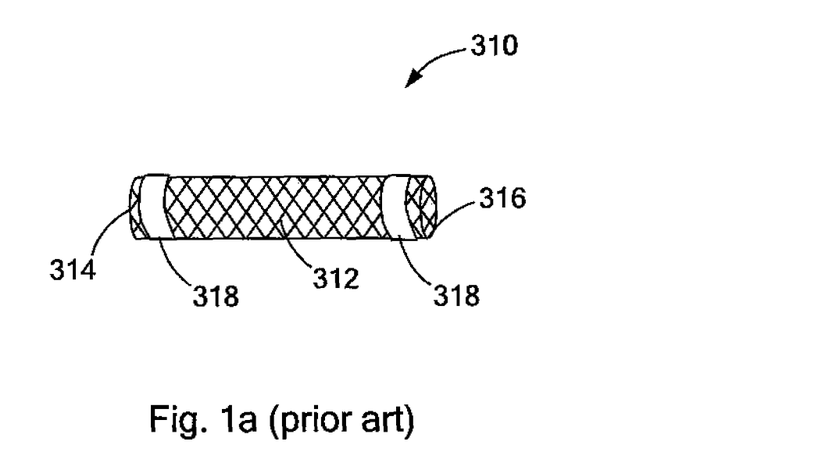
FIG. 1a is a side perspective view of a prior art occluding device, shown in a collapsed state.
Figure 1B:
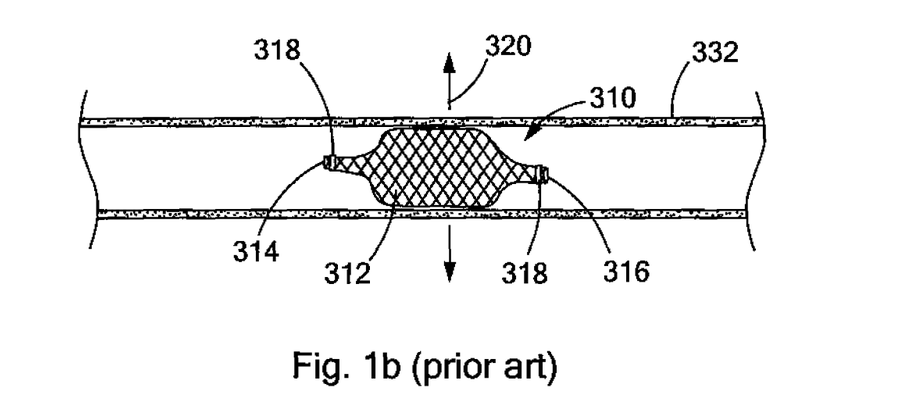
FIG. 1b is a side perspective view of the prior art occluding device of FIG. 1a, shown in an expanded state.

Another example of a vaso-occlusive device is an expandable occluding device 310 comprising an outer metal fabric surrounding an inner metal fabric, each comprising a plurality of braided metal strands 312, an example of which is shown in FIGS. 1a-b. The expandable occluding device 310 has proximal and distal ends 314, 316, each incorporating clamps 318 for securing the plurality of braided strands 312 that comprise the inner and outer metal fabrics together. The expandable occluding device 310 is shaped to create an occlusion of an abnormal opening in a vascular organ when in its expanded preset configuration, as illustrated in FIG. 1b. The expanded preset configuration is deformable to a lesser cross-section dimension for delivery through a channel in a patient's body, as illustrated in FIG. 1a. Both the outer and inner metal fabrics have a memory property such that the medical device tends to return to the expanded preset configuration when unconstrained. Accordingly, the expandable occluding device 310 remains in the expanded configuration which permits it to maintain a constant radially outward force in the direction of arrows 320 at the treatment site within the body vessel 322.

While occluding devices such as the previously described vaso-occlusive devices provide a number of advantages, they serve to hold the vessel open during embolization. Therefore, it is the material used for embolization that is important in effectively occluding blood flow and it is important to hold the material in place within the vessel. When vessels are large and/or flow is high, such devices may not be as effective. Thus, there exists a need for an improved occluding device.

BRIEF SUMMARY OF THE INVENTION

In satisfying the above need, as well as overcoming the enumerated drawbacks and other limitations of the related art, the present invention provides an improved occluding device for occlusion of fluid flow through a lumen of a body vessel having a vessel wall. The body vessel may include any cavity within the body, including but limited to aneurysms, blood vessels, and fistulas.

In one embodiment, the occlusion device includes an expandable tubular body having a tubular wall defining a lumen formed therethrough. The tubular wall has a proximal end extending to a distal end along a longitudinal axis of the tubular body. The tubular body includes a plurality of longitudinal slits formed through the tubular wall to define a plurality of flexible strips bound by a proximal non-slit portion at the proximal end and a distal non-slit portion at the distal end. The tubular body includes a plurality of barbs disposed on the flexible strips. The tubular body is configured to move between a collapsed state and an expanded state. The tubular body is configured to open radially to engage the barbs with the vessel wall defining the expanded state. The tubular body is configured to collapse along the longitudinal axis to draw the vessel wall radially inward defining the collapsed state. An occluding material configured to move between a collapsed state and an expanded state with the tubular body is housed within the lumen of the tubular body.

The present invention also encompasses a delivery assembly for delivering an occluding device described herein within a body vessel for occluding the body vessel. The assembly includes an outer sheath having a tubular wall extending from a proximal part to a distal part and defining a sheath lumen formed therethrough. An inner pusher member extends from a proximal portion to a distal portion and is disposed within the sheath lumen and configured for axial movement relative to the outer sheath. The occluding device is coaxially disposed within the sheath lumen and removably coupled to the distal portion of the inner pusher member and is deployable through the distal part of the outer sheath by means of the relative axial movement of the inner pusher member. The occluding device includes any of the devices described herein.

The present invention also includes a method of occluding fluid flow through a body vessel. The method includes introducing an outer sheath into the body vessel. The outer sheath has a tubular wall extending from a proximal part to a distal part and the tubular wall defines a sheath lumen formed therethrough. An inner pusher member extends from a proximal portion to a distal portion and is disposed within the sheath lumen and configured for axial movement relative to the outer sheath. Any one of the occluding devices described herein is coaxially disposed within the sheath lumen and is removably coupled to the distal portion of the inner pusher member. The method further includes advancing the outer sheath through the vessel until the distal part of the outer sheath is at a desired location in the vessel. The inner pusher member is then advanced to deliver the occluding device from the distal part of the outer sheath to the desired location in the vessel in the collapsed state. The method further includes expanding the occluding device to the expanded state, wherein the tubular body opens radially to engage the barbs with the vessel wall, and wherein the occluding material expands with the tubular body. The occluding device is then collapsed to the collapsed state, wherein the occluding material collapses with the tubular body, and wherein the barbs engaged with the vessel wall draw the vessel wall radially inward to occlude fluid flow through the body vessel.

Further objects, features and advantages of this invention will become readily apparent to persons skilled in the art after a review of the following description, with reference to the drawings and claims that are appended to and form a part of this specification.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF THE INVENTION

Figure 2:
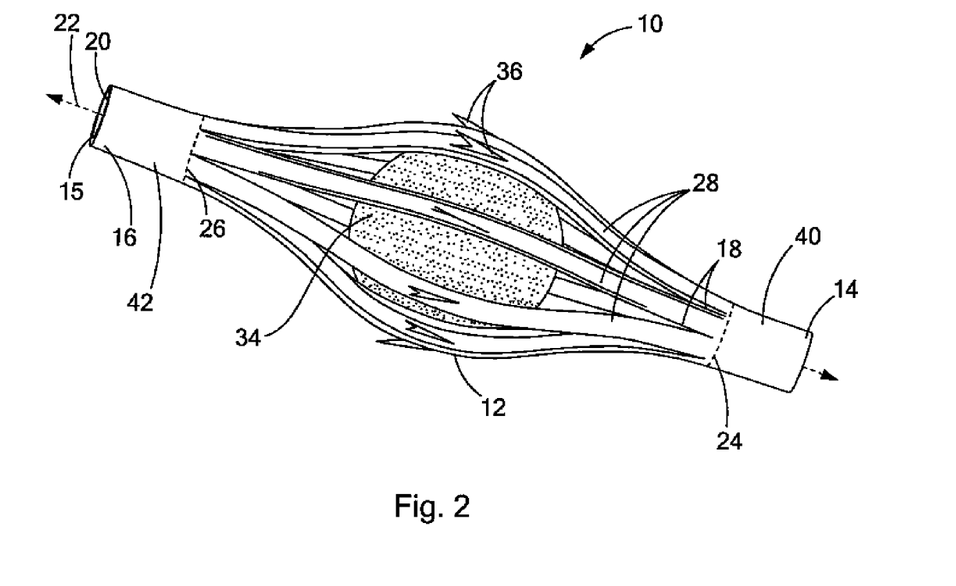
FIG. 2 is a side perspective view of an occluding device in accordance with an embodiment of the present invention, shown in an expanded state.

Referring now to FIG. 2, an embodiment of an occluding device for occluding a body vessel or another body lumen is illustrated therein and designated at 10. The occluding device 10 includes an expandable tubular body 12 having a tubular wall 15 defining a lumen 20 formed therethrough. The tubular wall 15 has a proximal end 16 extending to a distal end 14 along a longitudinal axis 22 of the tubular body 12. A plurality of longitudinal slits 18 is formed through the tubular wall 15 of the tubular body 12. In this embodiment, the slits 18 are preferably parallel with the longitudinal axis 22 and are formed along the tubular wall 15 from a point or radial location 24 proximal the distal end 14 to a point or radial location 26 distal the proximal end 16 such that the slits 18 do not extend along the entire length of the tubular body 12. As such, the plurality of slits 18 formed through the tubular wall 15 define a plurality of flexible strips 28 bound by distal and proximal non-slit portions or collars 40 and 42 at respective distal and proximal ends 14 and 16. The slits 18 may be formed via laser cutting or any other suitable means in the art.

As illustrated in FIG. 2, the occluding device 10 includes a plurality of barbs 36 disposed on the flexible strips 28. In this embodiment, the barbs 36 are preferably positioned along the flexible strips 28 about midway between the proximal and distal non-slit portions 42 and 40. Preferably, each flexible strip 28 includes at least one barb 36 configured to engage the vessel wall of the body vessel.

In this embodiment, the device 10 is configured to move between a collapsed state and an expanded state. As illustrated in FIG. 2, the tubular body 12 is shown in the expanded state, wherein the tubular body 12 is configured to open radially, i.e., the flexible strips 28 radially expand, to engage the barbs 36 with the vessel wall of the body vessel. In the collapsed state, the tubular body 12 includes a middle portion having a larger diameter than that of the proximal and distal non-slit portions 40 and 42. As described in more detail below with respect to the embodiments illustrated in FIGS. 3d and 4b, the occluding devices in accordance with the teachings of the present invention are configured to move from the expanded state to the collapsed state to pull the vessel wall radially inward once the barbs 36 have engaged the vessel wall. Accordingly, unlike many occluding devices known in the art, which expand the vessel and can lead to a recanalization path, the occluding devices of the present invention bring the vessel wall inward on itself, thus reducing the cross-sectional area of the vessel and thereby minimizing potential leaks and occluding fluid flow through the vessel.

As shown in FIG. 2, the occluding device 10 includes occluding material 34 housed within the lumen 20 of the tubular body 12. Preferably, the occluding material 34 is a sponge-form material configured to move between a collapsed state and an expanded state with the tubular body 12. In this embodiment, the occluding material 34 is preferably a cylindrical rod that is placed within the tubular body 12 in the collapsed state. Preferably, the cylindrical rod of occluding material 34 expands to occupy substantially the entire interior of the occluding device 10 in the radially expanded state. For illustration purposes, however, the occluding material 34 is illustrated in the Figures as having a spherical shape in the expanded configuration to more clearly illustrate the structure of the occluding device 10. The occluding material 34 can be made from extracellular matrix (ECM) material or other collagenous materials that have been subjected to processes that expand the materials. In certain forms, such expanded materials can be formed by the controlled contact of an ECM material with one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a graft device. Illustratively, the expanded material can be enriched with bioactive components, dried, and/or molded, etc., in the formation of a graft construct of a desired shape or configuration. In certain embodiments, a dried graft construct formed with the expanded ECM material can be highly compressible (or expandable) such that the material can be compressed for delivery, such as from within the lumen of a cannulated delivery device, and thereafter expand upon deployment from the device so as to become anchored within a patient and/or cause closure of a bodily segment within the patient.

Expanded collagenous or ECM materials can be formed by the controlled contact of a collagenous or ECM material with an aqueous solution or other medium containing sodium hydroxide. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

ECM materials that can be processed to make expanded materials can include any of those disclosed herein or other suitable ECM's. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the remodelable material can be in the range of about 0.5 to about 2 M, with a concentration of about 1 M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 1 M solution of NaOH having a pH of 14 at a temperature of about 37° C. for about 1.5 to 2 hours. Such treatment results in collagen denaturation and a substantial expansion of the remodelable material. Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g. 100 times magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100 times. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material. The more foamy and porous structure of an expanded ECM or other collagenous material can allow the material to be cast or otherwise prepared into a variety of three-dimensionally stable shapes for use in the preparation of medical materials and devices. It can further allow for the preparation of constructs that are highly compressible and which expand after compression. Such properties can be useful, for example, when the prepared graft construct is to be compressed and loaded into a deployment device (e.g. a lumen thereof) for delivery into a patient, and thereafter deployed to expand at the implant site.

After such alkaline treatments, the material can be isolated from the alkaline medium and processed for further use. Illustratively, the collected material can be neutralized and/or rinsed with water to remove the alkalinity from the material, prior to further processing of the material to form a graft construct.

A starting ECM material (i.e., prior to treatment with the alkaline substance) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment of the remodelable material with an alkaline substance will be sufficient to create a remodelable collagenous material which is substantially devoid of nucleic acids and lipids, and potentially also of growth factors, glycoproteins, glycosaminoglycans, and proteoglycans.

Most preferably, the extracellular matrix is comprised of small intestinal submucosa (SIS). SIS is a resorbable, acellular, naturally occurring tissue matrix composed of ECM proteins and various growth factors. SIS is derived from the porcine jejunum and functions as a remodeling bioscaffold for tissue repair. SIS has characteristics of an ideal tissue engineered biomaterial and can act as a bioscaffold for remodeling of many body tissues including skin, body wall, musculoskeletal structure, urinary bladder, and also supports new blood vessel growth. In many aspects, SIS is used to induce site-specific remodeling of both organs and tissues depending on the site of implantation. In theory, host cells are stimulated to proliferate and differentiate into site-specific connective tissue structures, which have been shown to completely replace the SIS material in time.

In this embodiment, the occluding or ECM material 34 is disposed within the lumen 20 of the tubular body 12 in a compressed or collapsed state and expands upon absorption of fluid which activates the clotting cascade. The ECM material 34 is foam-like and has shape memory such that upon expansion or swelling of water, saline, blood or other fluids, it expands to possibly ten times its original diameter and functions as a plug to effectively occlude fluid flow through the body vessel. The ECM material 34 has the ability to create a stasis within the vessel which activates the clotting cascade.

Preferably, the tubular body 12 is comprised of any suitable material such as a superelastic material, stainless steel, shape memory alloys, or other appropriate metallic alloys or polymers which are known to be suitable for use within the human body. Shape memory alloys, such as Nitinol, have the desirable property of becoming rigid, that is, returning to a remembered state, when heated above a transition temperature. Preferably, the tubular body 12 is a Nitinol cannula. The tubular body 12 may be heat set to the expanded state in which the tubular body 12 is programmed to radially expand, i.e., the flexible strips 28 expand radially outward from the longitudinal axis 22 of the tubular body 12. As such, the occluding device 10 preferably includes any suitable mechanical means known or contemplated in the art to contract or collapse the device 10 back to the collapsed state to pull the vessel wall inward on itself.

Alternatively, as described in more detail below with respect to FIGS. 3a-d, the occluding device may comprise mechanical means for expansion and contraction thereof. Referring to FIGS. 3a-d, an occluding device 110 in accordance with further teachings of the present invention is illustrated. The occluding device 110 is similar to that in FIG. 2, wherein similar components are denoted by similar reference numerals increased by 100. In this embodiment, the expansion and contraction means includes an elongate member 150, such as a screw or threaded wire guide or wire member. The wire 150 includes a threaded distal portion 154 extending to a threaded proximal portion 156 within the lumen 120 of the tubular body 112 and through the occluding material 134, i.e., the occluding material 134 may be packed or compressed around the wire 150.

Figure 3A:
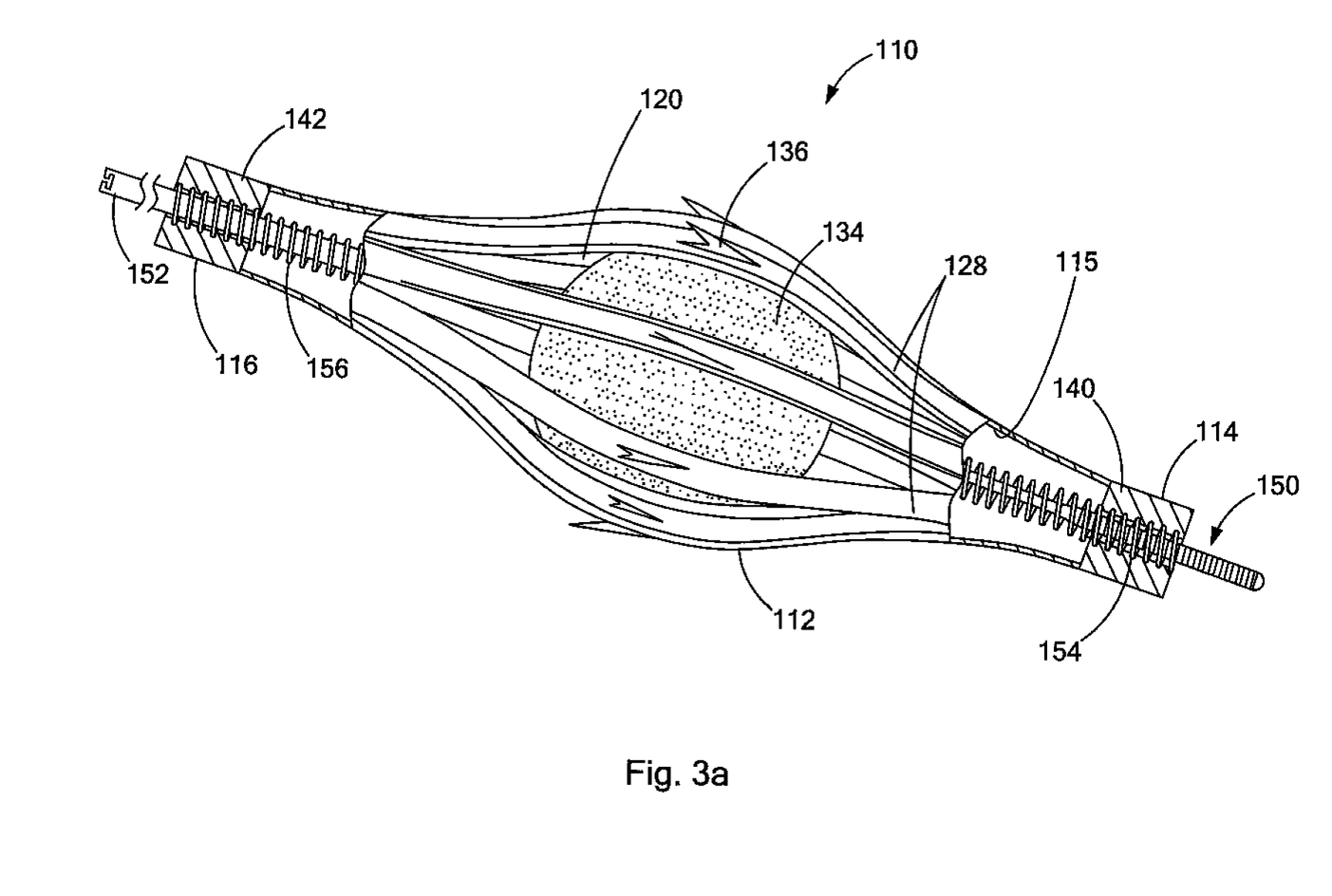
FIG. 3a is a side view, partially in cross-section, of an occluding device in accordance with another embodiment of the present invention.

In this embodiment, the threaded distal portion 154 is attached to the tubular body 112 at the distal non-slit portion 140 by any suitable means known in the art that allows rotational movement of the threaded wire 150. For example, as illustrated in FIG. 3a, the proximal and distal non-slit portions 142 and 140 define threaded proximal and distal end bores, respectively. In this embodiment, the threaded distal portion 154 of the wire 150 and the distal non-slit portion 140 of the tubular body 112 are cooperatively threaded to attachingly engage with one another. The threaded proximal portion 156 of the wire 150 and the proximal non-slit portion 142 of the tubular body 112 are likewise cooperatively threaded to engage with one another. In this embodiment, the proximal end 152 of the wire 150 is manipulated to rotate the wire 150 and engage the threaded proximal portion 156 with the proximal non-slit portion 140 to adjust the axial distance between the proximal and distal ends 116 and 114 of the tubular body 112 and thereby move the device 110 between the collapsed state and the expanded state.

Figure 3B:
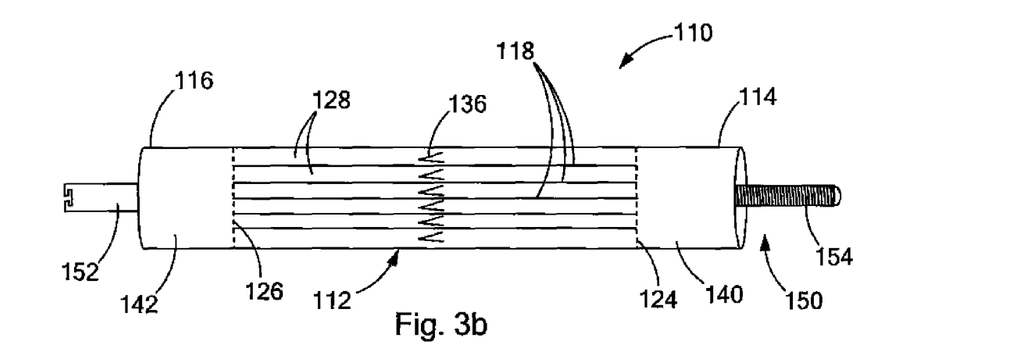
FIG. 3b is a side view of the occluding device of FIG. 3a, shown in a collapsed state.
Figure 3C:
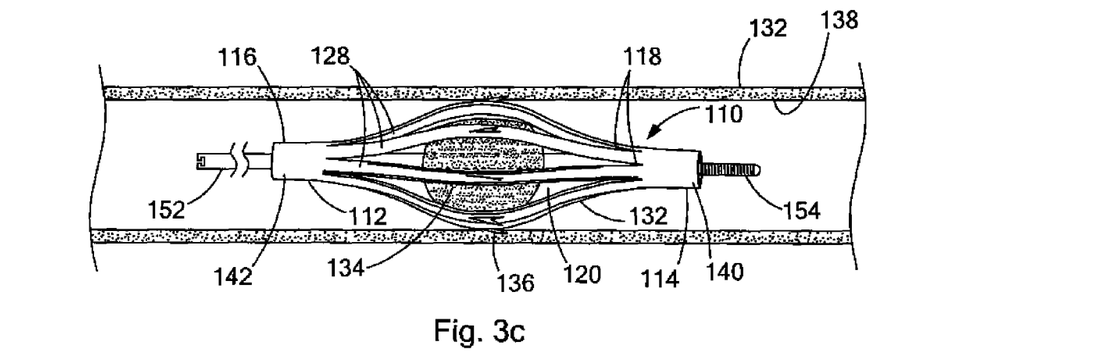
FIG. 3c is a side view of the occluding device of FIG. 3a, shown engaged with the vessel wall of the body vessel and in the expanded state.

In this embodiment, the device 110 is delivered to the desired site within the body vessel 132 in the collapsed state (FIG. 3b). Preferably, rotational movement of the wire 150 in an first direction is configured to engage the threaded proximal portion 156 of the wire 150 within the proximal non-slit portion 140 in a distal to proximal direction to shorten the axial distance between the proximal and distal ends 116 and 114 of the tubular body 112, thereby radially expanding the device 110 to the expanded state (FIG. 3c). As such, the device 110 is configured such that the threaded distal portion 154 of the wire 150 is longitudinally fixed relative to the distal non-slit portion 140, but allowed to rotate within the distal non-slit portion 140 of the tubular body 112 without becoming disengaged therefrom.

In another embodiment, instead of fixing or attaching the threaded distal portion 154 of the wire 150 within the distal non-slit portion 140, the proximal and distal non-slit portions 142 and 140 and the respective proximal and distal portions 156 and 154 of the wire 150 are oppositely threaded such that rotation of the wire 150 in a first direction causes the proximal and distal ends 116 and 114 to move towards one another into the radially expanded state, and rotation of the threaded wire 150 in an opposite second direction causes the proximal and distal ends 116 and 114 to move away from each other back into the radially collapsed state.

In a preferred embodiment, the occluding device 10 includes a means to mechanically expand and contract the tubular body 12. In this embodiment, the expansion means maintains the device 10 in the expanded state 32 and the barbs 36 engage the vessel wall 38. The device 10 is mechanically contracted to pull vessel wall tissue 38 radially inward once the barbs 36 have engaged the vessel wall 38. In one example, an expansion/contraction means includes threads at the proximal and distal ends, wherein one end can be fixed or threaded oppositely, and the other can be turned relative to the other end with precision to contract or expand the device 10.

Figure 3D:
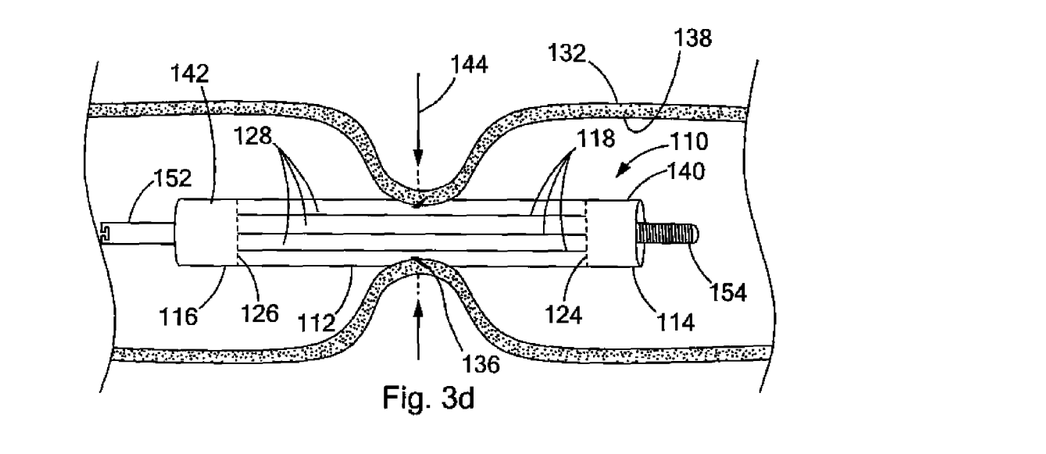
FIG. 3d is a side view of the occluding device of FIG. 3a, shown engaged with the vessel wall of the body vessel and in the collapsed state.

As shown in FIG. 3c, the barbs 136 engage with the vessel wall 138 when the device 110 is in the expanded state. In this embodiment, rotational movement of the wire 150 in an opposite second direction is configured to disengage the threaded proximal portion 156 of the wire 150 from within the proximal non-slit portion 140 in a proximal to distal direction to lengthen the axial distance between the proximal an distal ends 116 and 114 of the tubular body 112, thereby radially collapsing the device 110 to the collapsed state (FIG. 3d). As shown in FIG. 3d, as the device 110 is collapsed back into the collapsed state, the barbs 136, which are shown engaged within the vessel wall 138, pull the vessel wall 138 inward on itself to reduce the cross-sectional profile of the vessel 132. In the collapsed state, the occluding material 134 causes coagulation due to solid compression and acts as a plug to effectively occlude fluid flow through the vessel 132. Preferably, the collapse of the device 110 to contract the vessel 132 takes place within seconds or minutes.

Figure 4A:
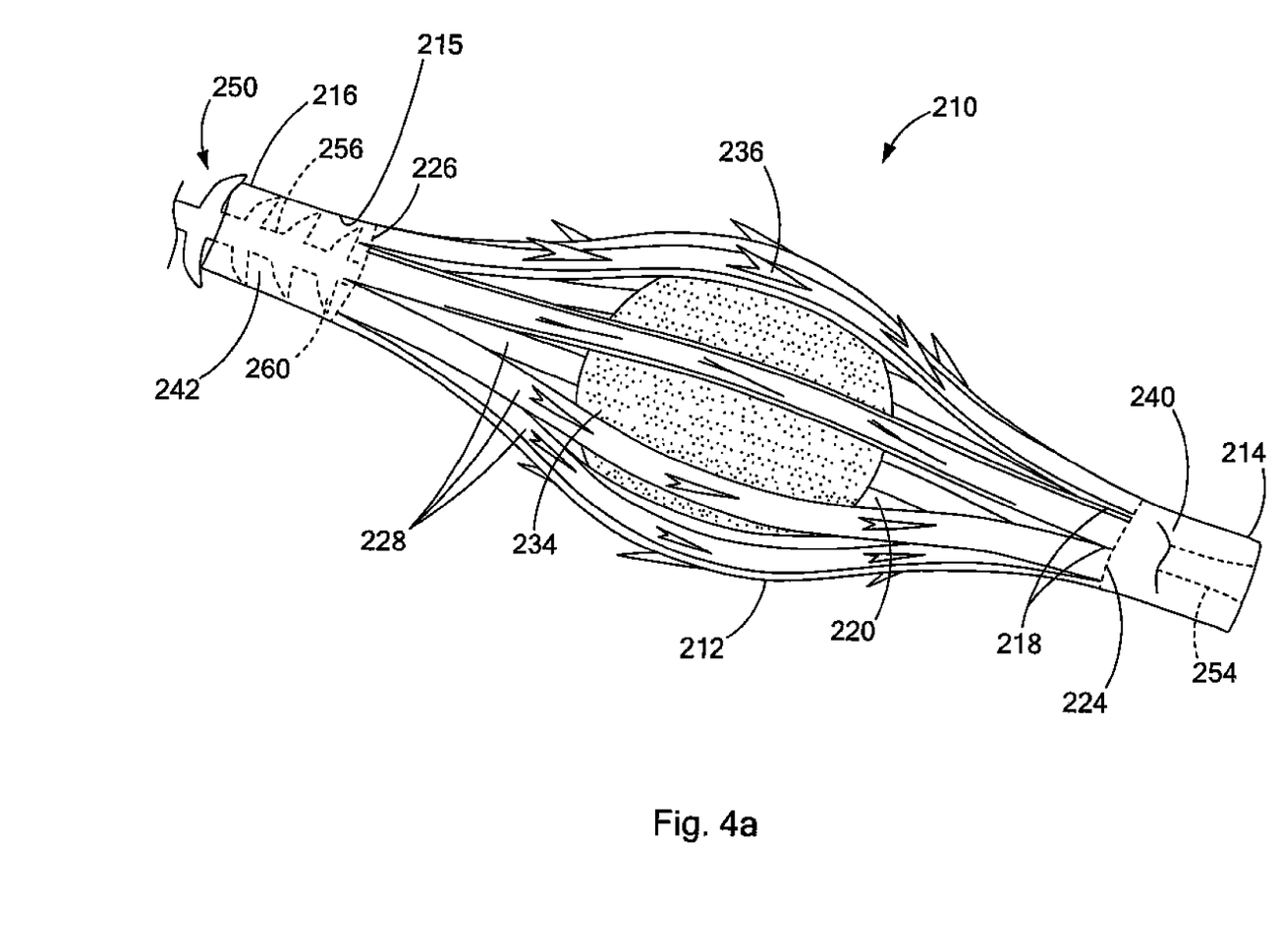
FIG. 4a is a side perspective view of an occluding device in accordance with yet another embodiment of the present invention.
Figure 4B:
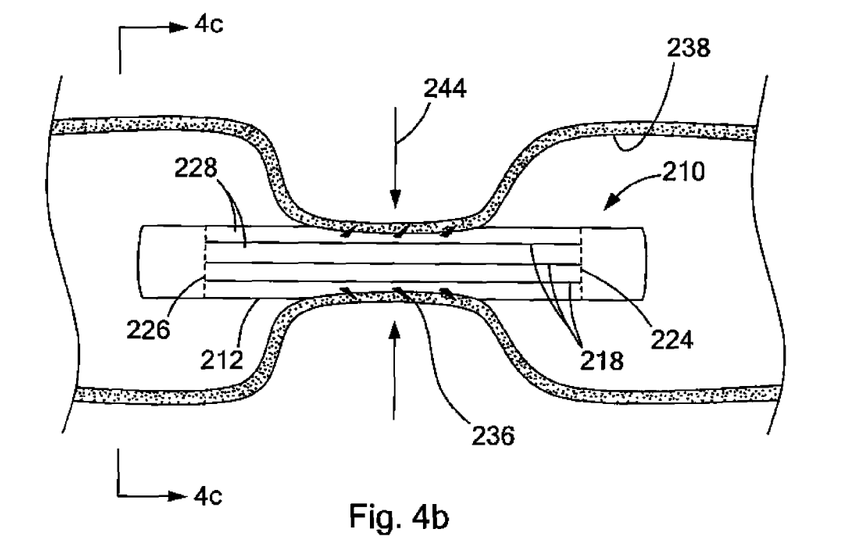
FIG. 4b is a side view of the occluding device of FIG. 4a, shown engaged with the vessel wall of the body vessel and in the collapsed state.
Figure 4C:
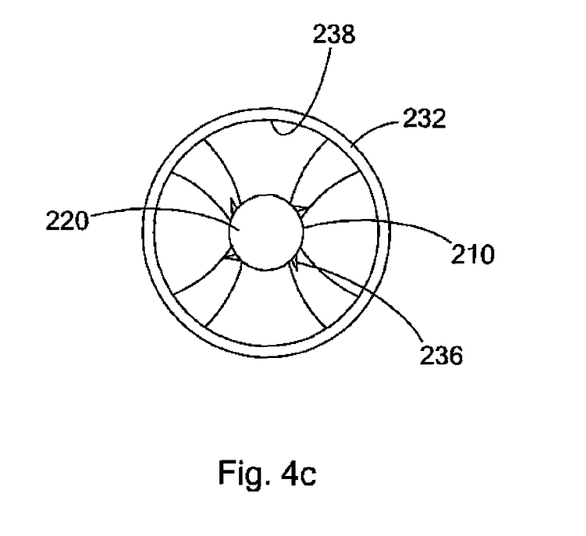
FIG. 4c is an end view of the occluding device of FIG. 4a, taken along line 4c-4c.

In another embodiment illustrated in FIGS. 4a-c, the tubular body 212 of the occluding device 210 is biased in the collapsed state. As such, the occluding device 210 includes mechanical means to expand the device 210 to the expanded state and the device 210 is biased to return to its remembered collapsed state. The occluding device 212 is similar to that in FIG. 2, wherein similar components are denoted by similar reference numerals increased by 200. In this embodiment, the expansion means includes an elongate member 250, such as a bioabsorbable suture or bioresorbable polymeric zip-tie. The suture 250 can be made from any suitable bioresorbable or bioabsorbable material known or contemplated by one of skill in the art. The suture 250 includes a distal portion 254 firmly attached to the distal non-slit portion 240 of the tubular body 212. The distal portion 254 of the suture 250 may be attached to the distal non-slit portion 240 of the tubular body 212 by any suitable means in the art, e.g., by an adhesive or mechanically fixing or tying the suture within the distal non-slit portion 240. The suture 250 extends from the distal portion 254 within the lumen 220 of the tubular body 212 and through the occluding material 234 to a proximal portion 256, i.e., the occluding material 234 may be packed or compressed around the suture 250.

As shown in FIG. 4a, the proximal portion 256 of the suture 250 includes a plurality of flexible flanges or tabs 260 configured to engage with the proximal non-slit portion 242 of the tubular body 212 to adjust the axial distance between the proximal and distal ends 216 and 214 of the tubular body 212 and thereby move the device from the collapsed state to the expanded state. In this embodiment, the device 210 is delivered to the desired site within the body vessel 232 in the collapsed state. Preferably, the suture 250 is retracted in a distal to proximal direction to engage one of the tabs 260 with the proximal non-slit portion 242 of the tubular body 212. As shown in FIG. 4a, the tubular wall 215 of the tubular body 212 maintains the flexible tabs 260 in a compressed state within the lumen 220 of the proximal non-slit portion 242 of the tubular body 212. As the suture 250 is proximally retracted, the distal end 214 of the tubular body 212 is moved toward the proximal end 216 of the tubular body, thereby shortening the axial distance between the proximal and distal ends 216 and 214 and radially expanding the device to the expanded state.

In this embodiment, proximal retraction of the suture 250 via a pusher member, as discussed in more detail below, allows the tabs 260 to exit the proximal end 216 of the tubular body 212 and, as the compression force of the tubular wall 215 is relieved, the tabs 260 expand to a dimension larger than the diameter of the proximal non-slit portion 242 of the tubular body 212. The tabs 260 thus maintain the position of the distal end 214 of the tubular body 212 relative to the proximal end 216 in the expanded state. The tabs 260 are positioned along the proximal portion 256 of the suture 250 a predetermined distance from the distal portion 254 of the suture 250 relative to the axial length of the tubular body 212 such that engagement of one of the tabs 260 with the proximal end 216 of the tubular body 212 provides the middle portion of the tubular body 212 with an enlarged diameter relative to the proximal and distal ends 216 and 214 in the radially expanded state. In the expanded state, the barbs 236 engage the vessel wall 238 and anchor the device 210 in place within the vessel 232.

In this embodiment, the suture 250 resorbs over time allowing the device 210 to return to its remembered collapsed state. Without the suture 250 maintaining the shortened axial distance between the proximal and distal ends 216 and 214 of the tubular body 212, and thus the radially expanded state, the device 210 returns to the remembered collapsed state, thereby lengthening the axial distance between the proximal and distal ends 216 and 214 of the tubular body 212. As shown in FIG. 4b, the suture 250 has been resorbed and the device 210 has reverted back into the collapsed state. In this embodiment, there are three barbs 236 disposed along the flexible strips 228, each of which is shown engaged within the vessel wall 238. As shown in FIG. 4c, the barbs 236 pull the vessel wall 238 inward on itself as the device 210 reverts to the collapsed state to reduce the cross-sectional profile of the vessel 232. In the collapsed state, the occluding material 234 causes coagulation due to solid compression and acts as a plug to effectively occlude fluid flow through the vessel 232. Preferably, the collapse of the device 210 to contract the vessel 232 takes place within seconds or minutes.

Not only do the occluding devices of the present invention provide enhanced occlusion of fluid through the body vessel by contracting the vessel, occluding devices of the present invention require a smaller amount of occluding material to effectively occlude the vessel in comparison to prior art occluding devices which enlarge the vessel.

Figure 5A:
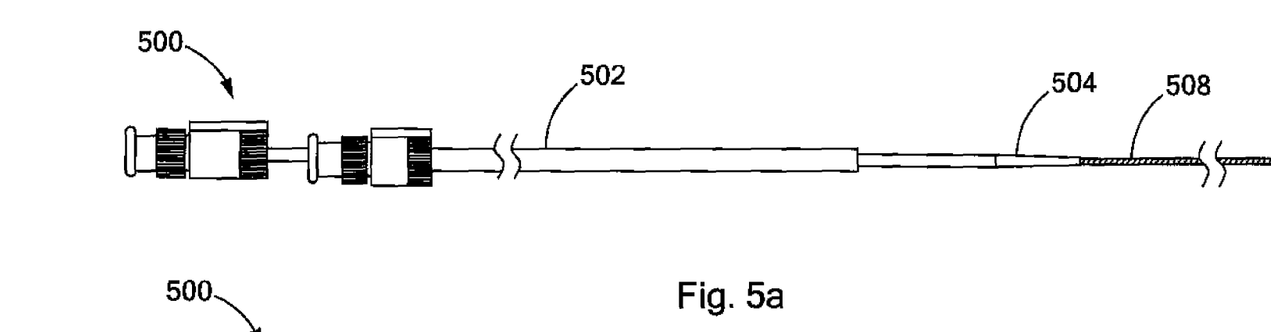
FIG. 5a is a side view of a delivery assembly for use with the occluding device, in accordance with the principles of the present invention.
Figure 5B:
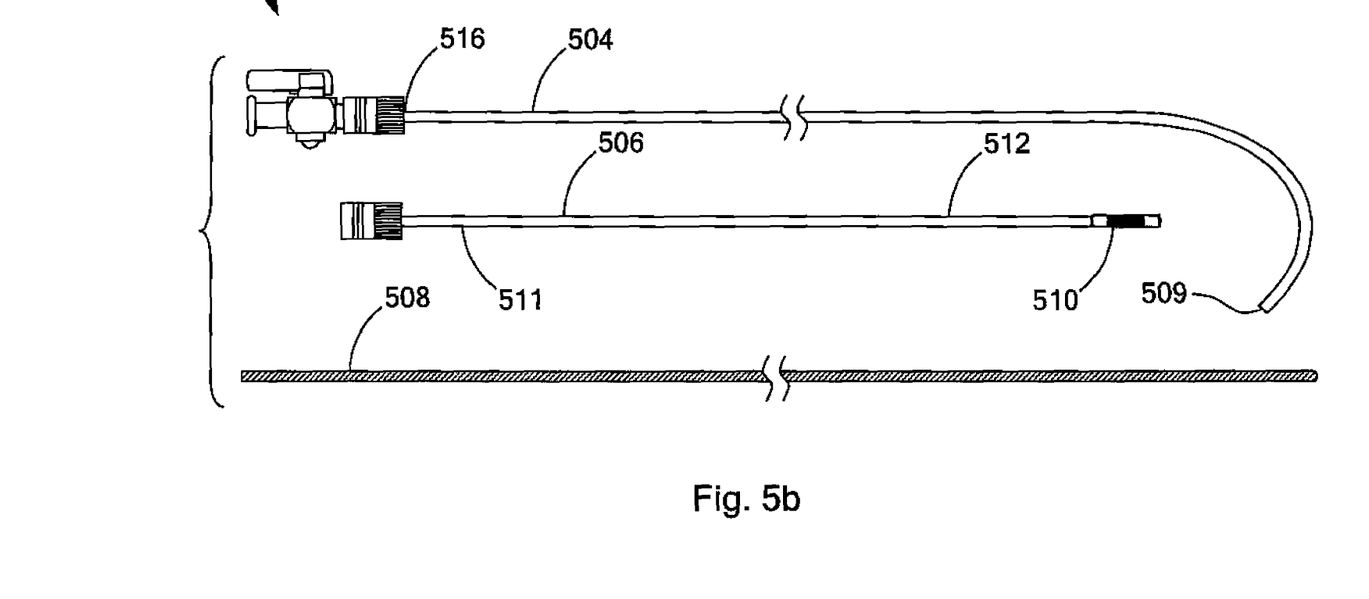
FIG. 5b is an exploded view of the delivery assembly of FIG. 5a, in accordance with the principles of the present invention.

FIGS. 5a and 5b depict a delivery assembly 500 for introducing and retrieving the occluding device for occluding a body vessel in accordance with another embodiment of the present invention. As shown, the delivery assembly 500 includes a polytetrafluoroethylene (PTFE) introducer sheath 502 for percutaneously introducing an outer sheath 504 into a body vessel. Of course, any other suitable material for the introducer sheath 502 may be used without falling beyond the scope or spirit of the present invention. The introducer sheath 502 may have any suitable size, for example, between about three-french to eight-french. The introducer sheath 502 serves to allow the outer sheath 504 and an inner catheter or pusher member 506 to be percutaneously inserted to a desired location in the body vessel. The inner member may also include, for example, a stylet. The introducer sheath 502 receives the outer sheath 504 and provides stability to the outer sheath 504 at a desired location of the body vessel. For example, the introducer sheath 502 is held stationary within a common visceral artery, and adds stability to the outer sheath 504, as the outer sheath 504 is advanced through the introducer sheath 502 to an occlusion area in the vasculature. The outer sheath 504 has a body extending from a proximal end 516 to a distal end 509, the body being tubular and including a sheath lumen extending therethrough.

As shown, the assembly 500 may also include a wire guide 508 configured to be percutaneously inserted within the vasculature to guide the outer sheath 504 to the occlusion area. The wire guide 508 provides the outer sheath 504 with a path to follow as it is advanced within the body vessel. The size of the wire guide 508 is based on the inside diameter of the outer sheath 504 and the diameter of the target body vessel.

When the distal end 509 of the outer sheath 504 is at the desired location in the body vessel, the wire guide 508 is removed and the occluding device 510, having a proximal end contacting a distal portion 512 of the inner pusher member 506, is inserted into the outer sheath 504. The inner pusher member 506 is advanced through the outer sheath 504 for deployment of the occluding device 510 through the distal end 509 to occlude the body vessel during treatment of, for example, an aneurism, or to otherwise occlude a body vessel. The inner pusher member 506 extends from a proximal portion 511 to a distal portion 512 and is configured for axial movement relative to the outer sheath 504. In this example, the distal portion 512 is shown adjacent to an occluding device 510 (similar to any of the occluding devices described above). Thus, before deployment, the occluding device 510 is coaxially disposed within the lumen of the outer sheath 504 and removably coupled to the distal portion 512 of the inner pusher member 506.

For example, the distal portion 512 of the inner pusher member 506 is preferably coupled to the proximal end 152 of the wire 150 of the occluding device 110 illustrated in FIGS. 3a-d. In this embodiment, the distal portion 512 of the pusher member 506 and the proximal end 152 of the wire 150 may have corresponding male and female attachment members to releasably couple the pusher member 506 and the wire 150 to one another for manipulation of the wire 150 during expansion and contraction of the occluding device 110. Alternatively, the distal portion 512 of the inner pusher member 506 may include a grasping member for releasably grasping and manipulating the suture 250 of the occluding device 210 illustrated in FIGS. 4a-c.

The outer sheath 504 further has a proximal end 516 and a hub 555 to receive the inner pusher member 506 and occluding device 510 to be advanced therethrough. The size of the outer sheath 504 is based on the size of the body vessel in which it percutaneously inserts, and the size of the occluding device 510.

In this embodiment, the occluding device 510 and inner pusher member 506 are coaxially advanced through the outer sheath 504, following removal of the wire guide 508, in order to position the occluding device 510 to occlude the body vessel. The occluding device 510 is guided through the outer sheath 504 by the inner pusher member 506, preferably from the hub 555, and exits from the distal end 509 of the outer sheath 504 at a location within the vasculature where occlusion is desired. Thus, the occluding device 510 is deployable through the distal end 509 of the outer sheath 504 by means of axial relative movement of the inner pusher member 506. In order to more easily deploy the occluding device 510 into the body vessel, the occluding device 510 may have a slippery coating, such as Silicone or slipcoating.

Likewise, this embodiment may also retrieve the occlusion device 510 by positioning the distal end 509 of the outer sheath 504 adjacent the deployed device 510 in the vasculature. The inner pusher member 506 is advanced through the outer sheath 504 until the distal portion 512 protrudes from the distal end 509 of the outer sheath 504. The distal portion 512 is coupled to a proximal end of the occluding device 510, after which the inner pusher member 506 is retracted proximally, drawing the occluding device 510 into the outer sheath 504.

It is understood that the assembly described above is merely one example of an assembly that may be used to deploy the occluding device in a body vessel. Of course, other apparatus, assemblies and systems may be used to deploy any embodiment of the occlusion device without falling beyond the scope or spirit of the present invention.

Figure 6:
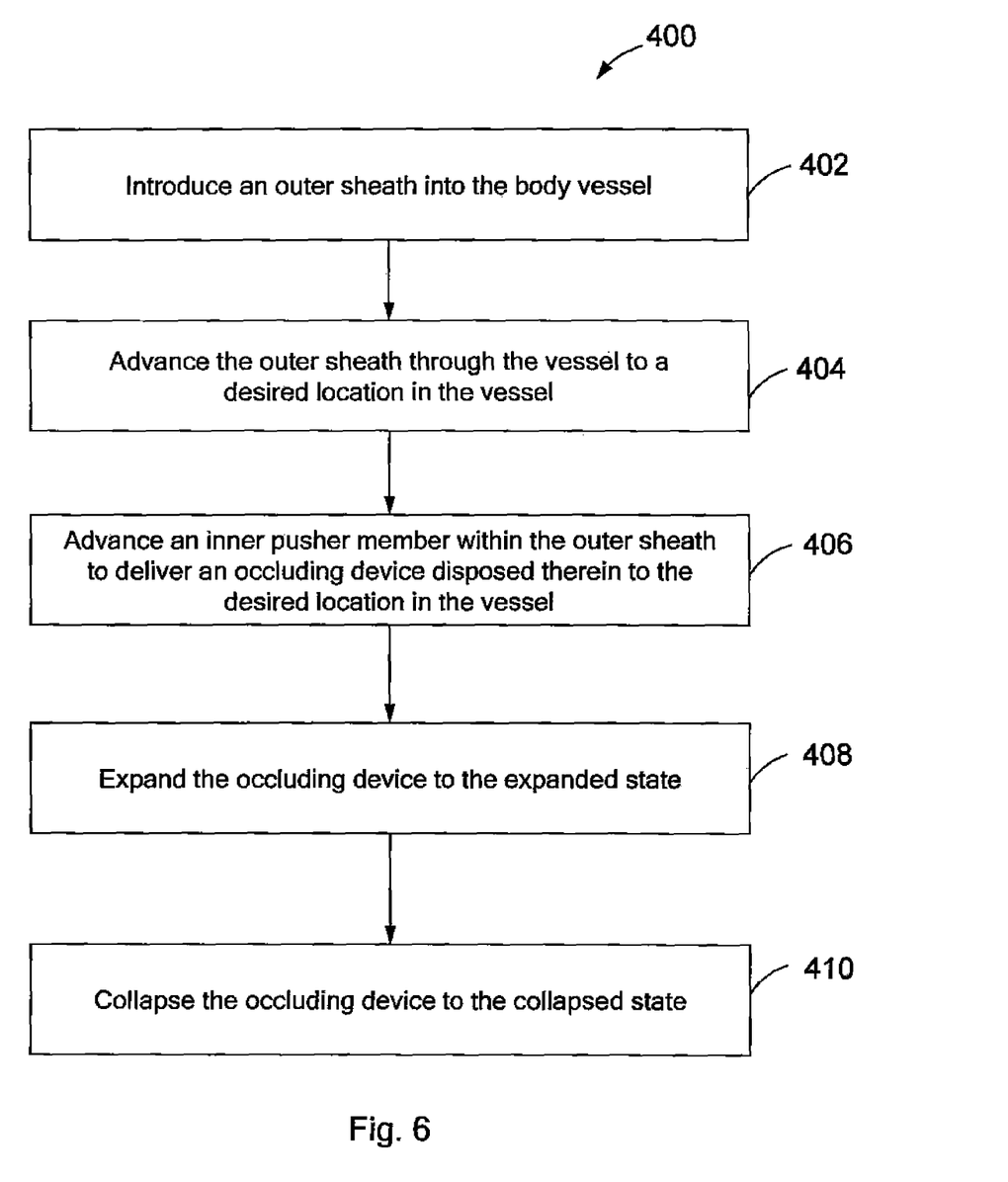
FIG. 6 is a block diagram describing a method of occluding fluid flow through a body vessel in accordance with the principles of the present invention.

Turning to FIG. 6, the present invention further provides a method 400 of occluding fluid flow through a body vessel. The method 400 includes introducing (402) an outer sheath into the body vessel and advancing (404) the outer sheath through the body vessel to a desired location in the vessel. The method 400 further includes advancing (406) an inner pusher member within the outer sheath to deliver an occluding device, in accordance with any of the embodiments disclosed herein, disposed within the outer sheath to the desired location in the vessel. The method 400 further includes expanding (408) the occluding device to the expanded state and collapsing (410) the occluding device to the collapsed state, wherein the occluding device pulls the vessel wall inward on itself and occludes fluid flow through the vessel.

As a person skilled in the art will readily appreciate, the above description is meant as an illustration of implementation of the principles this invention. This description is not intended to limit the scope or application of this invention in that the invention is susceptible to modification, variation and change, without departing from the spirit of this invention, as defined in the following claims.

The invention claimed is:

1. An occluding device for occlusion of fluid flow through a lumen of a body vessel having a vessel wall, the device comprising:
an expandable tubular body having a tubular wall defining a lumen formed therethrough, the tubular wall having a proximal end extending to a distal end along a longitudinal axis of the tubular body, the tubular body including a plurality of longitudinal slits formed through the tubular wall to define a plurality of flexible strips bound by a proximal non-slit portion at the proximal end and a distal non-slit portion at the distal end, the tubular body including a plurality of barbs disposed on the flexible strips, the tubular body being configured to move between a collapsed state and an expanded state, the tubular body being configured to open radially to engage the barbs with the vessel wall defining the expanded state and to collapse along the longitudinal axis to draw the vessel wall radially inward defining the collapsed state;
occluding material housed within the lumen of the tubular body, wherein the occluding material is configured to move between a collapsed state and an expanded state with the tubular body; and
an expander to expand the tubular body, the expander comprising an elongate member disposed within the lumen of the tubular body and through the occluding material, the elongate member having a distal portion attached to the distal non-slit portion of the tubular body extending to a proximal portion configured to engage with the proximal non-slit portion of the tubular body to adjust the axial distance between the proximal and distal ends of the tubular body and move the device from the collapsed state to the expanded state wherein the elongate member is a resorbable suture having a plurality of flexible expandable tabs at the proximal portion.

2. The occluding body of claim 1, wherein the flexible tabs are compressed within the proximal non-slit portion of the tubular body, and wherein as the resorbable suture is proximally retracted, at least one of the flexible tabs exits the proximal non-slit portion and expands to engage the proximal non-slit portion to adjust the axial distance between the proximal and distal ends of the tubular body.

3. The occluding body of claim 1, wherein the tubular body is biased to return to the collapsed state after the suture is resorbed within the body vessel.

4. The occluding device of claim 1, wherein the plurality of barbs includes at least one barb disposed on the flexible strips at about midway between the proximal and distal non-slit portions.

5. The occluding device of claim 1, wherein the tubular body comprises nitinol.

6. The occluding device of claim 1, wherein the occluding material comprises one of a remodelable material and a synthetic material, wherein the remodelable material comprises one of an extracellular matrix material and an absorbable material.

7. The occluding device of claim 6, wherein the extracellular matrix comprises small intestine submucosa.

8. The occluding device of claim 1, wherein the occluding material is a cylindrical rod within the tubular body.

9. The occluding device of claim 1, wherein the occluding material occupies substantially the entire interior volume of the occluding device in the radially expanded state.

10. The occluding device of claim 1, wherein the proximal non-slit portion has a first diameter and the distal non-slit portion has a second diameter, the first diameter being the same as the second diameter.

11. The occluding device of claim 10, wherein the tubular body comprises a middle portion having a middle diameter, the middle diameter being larger than the first diameter in the expanded state.

12. A delivery assembly for delivering an occluding device within a body vessel for occluding the body vessel, the assembly comprising:
an outer sheath having a tubular wall extending from a proximal part to a distal part, the tubular wall defining a sheath lumen formed therethrough;
an inner pusher member extending from a proximal portion to a distal portion, the inner member being disposed within the sheath lumen and configured for axial movement relative to the outer sheath;
the occlusion device being coaxially disposed within the sheath lumen and removably coupled to the distal portion of the inner pusher member and deployable through the distal part of the outer sheath by means of the relative axial movement of the inner pusher member, the occluding device comprising:
an expandable tubular body having a tubular wall defining a lumen formed therethrough, the tubular wall having a proximal end extending to a distal end along a longitudinal axis of the tubular body, the tubular body including a plurality of longitudinal slits formed through the tubular wall to define a plurality of flexible strips bound by a proximal non-slit portion at the proximal end and a distal non-slit portion at the distal end, the tubular body including a plurality of barbs disposed on the flexible strips, the tubular body being configured to move between a collapsed state and an expanded state, the tubular body being configured to open radially to engage the barbs with the vessel wall defining the expanded state and to collapse along the longitudinal axis to draw the vessel wall radially inward defining the collapsed state; and occluding material housed within the lumen of the tubular body, wherein the occluding material is configured to move between a collapsed state and an expanded state with the tubular body; and an expander to expand the tubular body, the expander comprising an elongate member disposed within the lumen of the tubular body and through the occluding material, the elongate member having a distal portion attached to the distal non-slit portion of the tubular body extending to a proximal portion configured to engage with the proximal non-slit portion of the tubular body to adjust the axial distance between the proximal and distal ends of the tubular body and move the device from the collapsed state to the expanded state wherein the elongate member is a resorbable suture having a plurality of flexible expandable tabs at the proximal portion.

13. The delivery assembly of claim 12, wherein the flexible tabs are compressed within the proximal non-slit portion of the tubular body, and wherein as the resorbable suture is proximally retracted, at least one of the flexible tabs exits the proximal non-slit portion and expands to engage the proximal non-slit portion to adjust the axial distance between the proximal and distal ends of the tubular body.

14. The delivery assembly of claim 12, wherein the tubular body is biased to return to the collapsed state after the suture is resorbed within the body vessel.

15. The delivery assembly of claim 12, wherein the tubular body comprises nitinol.

16. The delivery assembly of claim 12, wherein the occluding material comprises one of a remodelable material and a synthetic material, wherein the remodelable material comprises one of an extracellular matrix material and an absorbable material.

17. The delivery assembly of claim 12, wherein the occluding material is a cylindrical rod within the tubular body.

18. The delivery assembly of claim 12, wherein the occluding material occupies substantially the entire interior volume of the occluding device in the radially expanded state.

19. The delivery assembly of claim 12, wherein the proximal non-slit portion has a first diameter and the distal non-slit portion has a second diameter, the first diameter being the same as the second diameter.

20. The delivery assembly of claim 19, wherein the tubular body comprises a middle portion having a middle diameter, the middle diameter being larger than the first diameter in the expanded state.

* * * * *